United States Patent
Jang et al.

(10) Patent No.: US 10,653,591 B2
(45) Date of Patent: May 19, 2020

(54) LIQUID OIL-DISPERSIBLE TYPE EYE MAKEUP COMPOSITION

(71) Applicant: AMOREPACIFIC CORPORATION, Seoul (KR)

(72) Inventors: Soon Hui Jang, Yongin-si (KR); Eun Sil Han, Yongin-si (KR)

(73) Assignee: AMOREPACIFIC CORPORATION, Seoul (KR)

( * ) Notice: Subject to any disclaimer, the term of this patent is extended or adjusted under 35 U.S.C. 154(b) by 0 days.

(21) Appl. No.: 15/764,756

(22) PCT Filed: Sep. 27, 2016

(86) PCT No.: PCT/KR2016/010795
§ 371 (c)(1),
(2) Date: Mar. 29, 2018

(87) PCT Pub. No.: WO2017/057888
PCT Pub. Date: Apr. 6, 2017

(65) Prior Publication Data
US 2018/0318182 A1    Nov. 8, 2018

(30) Foreign Application Priority Data

Sep. 30, 2015  (KR) ........................ 10-2015-0137394

(51) Int. Cl.
| | | |
|---|---|---|
| *A61K 8/06* | (2006.01) | |
| *A61Q 1/10* | (2006.01) | |
| *A61K 8/891* | (2006.01) | |
| *A61K 8/31* | (2006.01) | |
| *A61K 8/92* | (2006.01) | |
| *A61Q 19/00* | (2006.01) | |
| *A61K 8/81* | (2006.01) | |
| *A61K 8/89* | (2006.01) | |
| *A61K 8/91* | (2006.01) | |

(52) U.S. Cl.
CPC ................ *A61K 8/06* (2013.01); *A61K 8/31* (2013.01); *A61K 8/81* (2013.01); *A61K 8/89* (2013.01); *A61K 8/891* (2013.01); *A61K 8/91* (2013.01); *A61K 8/92* (2013.01); *A61Q 1/10* (2013.01); *A61Q 19/00* (2013.01)

(58) Field of Classification Search
CPC . A61K 8/31; A61K 8/891; A61K 8/92; A61K 8/895; A61K 8/89; A61Q 1/10; A61Q 19/00
See application file for complete search history.

(56) References Cited

U.S. PATENT DOCUMENTS

| | | |
|---|---|---|
| 5,061,481 A | 10/1991 | Suzuki et al. |
| 6,689,345 B2 | 2/2004 | Lezer |
| 7,189,388 B2 | 3/2007 | Auguste et al. |
| 9,132,078 B2 | 9/2015 | Najdek et al. |
| 2005/0031561 A1* | 2/2005 | Patil .............. A61K 8/585 424/63 |
| 2006/0078578 A1* | 4/2006 | Sandewicz ........... A61K 8/26 424/401 |
| 2015/0004116 A1 | 1/2015 | Tan et al. |
| 2015/0056152 A1 | 2/2015 | Masuda et al. |

FOREIGN PATENT DOCUMENTS

| | | |
|---|---|---|
| JP | 62298512 A | 12/1987 |
| JP | 02025411 A | 1/1990 |
| JP | 07196449 A | 8/1995 |
| JP | 08143426 A | 6/1996 |
| JP | 2003-055158 A | 2/2003 |
| JP | 2009114099 A | 5/2009 |
| JP | 2009227592 A | 10/2009 |
| JP | 2011213645 A | 10/2011 |
| JP | 2013063919 A | 4/2013 |
| JP | 2013209340 A | 10/2013 |
| JP | 2015063512 A | 4/2015 |
| KR | 10-2001-0014003 A | 2/2001 |
| KR | 10-2003-0050531 A | 6/2003 |
| KR | 20030050531 A * | 6/2003 |
| KR | 10-0404641 B1 | 11/2003 |
| KR | 10-2004-0071810 A | 8/2004 |
| KR | 10-2006-0128361 A | 12/2006 |
| KR | 10-1060805 B1 | 8/2011 |
| KR | 10-2013-0031037 A | 3/2013 |
| WO | 95/03776 A1 | 2/1995 |

OTHER PUBLICATIONS

KR-20030050531-A, Espacenet English translation, downloaded in Jun. 2019 (Year: 2019).*
The extended European search report, Application No. 16852034.4, dated Jun. 13, 2018.
International Search Report for International Application No. PCT/KR2016/010795. (2 Pages) (dated Jan. 13, 2017).

* cited by examiner

*Primary Examiner* — Mark V Stevens
(74) *Attorney, Agent, or Firm* — Lucas & Mercanti, LLP

(57) ABSTRACT

The present invention provides a liquid oil-dispersible type eye makeup composition having: a volatile oil; a hard-type film forming agent; and a soft-type film forming agent. The eye makeup composition of the present invention forms a solid and flexible film layer so as to be lightly spread and have excellent lasting properties, and is also quickly dried and has little fallout, thereby enabling the feeling of use to be remarkably improved over that of a conventional eye makeup composition.

9 Claims, 1 Drawing Sheet

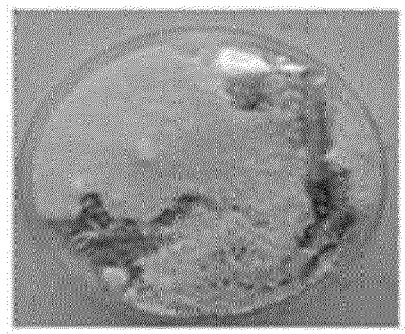 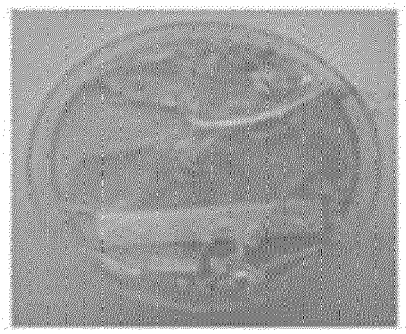 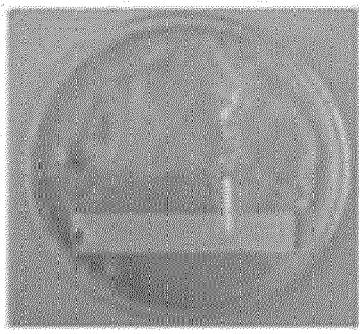
100:0　　　　　　　70:30　　　　　　　60:40
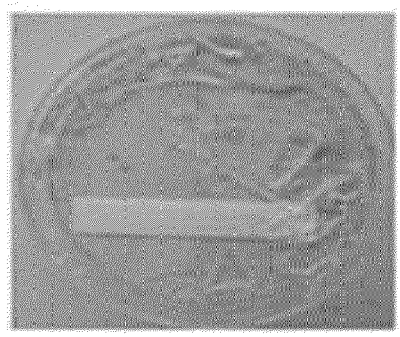 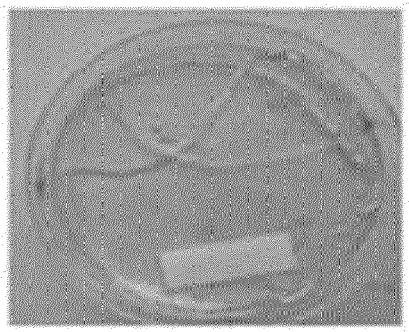 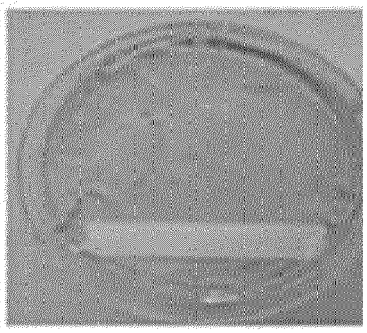
50:50　　　　　　　30:70　　　　　　　0:100

LIQUID OIL-DISPERSIBLE TYPE EYE MAKEUP COMPOSITION

CROSS-REFERENCE TO RELATED APPLICATIONS

This application is a 371 of PCT/KR2016/010795, filed Sep. 27, 2016 which claims the benefit of Korean Patent Application No. 10-2015-0137394, filed Sep. 30, 2015 the contents of each of which are incorporated herein by reference.

TECHNICAL FIELD

The present invention relates to a liquid oil-dispersible type eye makeup composition, specifically which can be variously applied to the preparation of eye makeup compositions including mascara, eyeliner and the like and to other similar fields.

BACKGROUND ART

According to the changes in the hot and humid climates and in the makeup trends that pursue practicality, a light feeling of use is increasingly required in relation to eye makeup compositions. Particularly, in the case of formulations such as mascara or eyeliner which is used routinely, there is also a growing need for sustainability capable of maintaining the initial makeup state for a long time without blurring or being disordered, in addition to the light feeling of use.

As one way to meet this need, the eye makeup compositions have been conventionally prepared as liquid oil-dispersible formulations. This is because, generally, in the case of water-in-oil type composition, the effect of giving various functions is excellent, but there are disadvantages that stickiness occurs and sustainability against sebum is weak, and in the case of an oil-in-water type composition, it is lightweight compared to the water-in-oil type, but it has a disadvantage that the water proof property is poor. Therefore, the eye makeup composition was provided as a liquid oil-dispersible formulation comprising of a mixture of oils, pigment and a film forming agent. In this case, it was intended to implement the light feeling of use by using highly volatile oil and secure the sustainability through the film forming agent.

However, the film-forming agents used in the conventional oil-dispersible formulations is a hard type film forming agent and thus have the limitation that it is difficult to satisfy both the light feeling of use and the sustainability required in the eye makeup. This is because the characteristics of the film layer are directly changed depending on the ratio of the MQ resin constituting the hard type film forming agent. That is, when the M/Q ratio is high, an excessively hard film layer is formed and thus easily broken, thereby resulting in dusting and thus deteriorating the sustainability, and when the M/Q ratio is low, a too soft film layer is formed and thus it is damp and sticky and heavily applied, thereby reducing the feeling of use.

As a result of extensive studies in view of the above, the inventors of the present invention have identified that, by using a volatile oil, and a mixture of a hard type film forming agent and a soft type film forming agent, it is possible to provide an eye makeup composition with a significantly improved overall feeling of use. Furthermore, the inventors of the present invention have completed the present invention by specifically confirming the optimum composition of each of the above components, the range of the optimum M/Q ratio of a hard type film forming agent when used in combination with a soft type film forming agent and so on.

PRIOR ART LITERATURE

Korean Patent No. 1060805, "Long lasting Water-Proof Eye Make-Up Composition"

DISCLOSURE

Technical Problem

Therefore, it is an object of the present invention to provide an eye makeup composition that simultaneously satisfies a light feeling of use and an excellent sustainability.

Technical Solution

According to an object of the present invention, the present invention provides a liquid oil-dispersible type eye makeup composition comprising a volatile oil; a hard type film forming agent; and a soft type film forming agent.

Specifically, a silicone-based film forming agent may be preferably used as the hard type film forming agent, and more preferably, the M/Q ratio of the MQ resin comprising the silicone-based film forming agent may be 0.8 or less (wherein $M=R_3SiO_{1/2}$, $Q=SiO_2$, R=alkyl group having 1 to 8 carbon atoms or aryl group).

In addition, a silicone graft acrylic polymer-based film forming agent may be preferably used as the soft type film forming agent.

Meanwhile, the volatile oil does not contain water and an aqueous component. Preferably, a volatile hydrocarbon oil, a volatile silicone oil or a mixture thereof can be used.

Advantageous Effects

By using the above-described technical solution means, the eye makeup composition of the present invention can form a hard and flexible film layer. As a result, improved spreadability, sustainability and drying speed are exhibited, and the powder dropping phenomenon is improved, and thus the feeling of use is excellent.

DESCRIPTION OF DRAWINGS

FIG. 1 is a photograph comparing the shapes of film layers produced depending on the mixing ratio of the hard type film forming agent and the soft type film forming agent.

BEST MODE

The present invention provides a liquid oil-dispersible type eye makeup composition comprising a volatile oil; a hard type film forming agent; and a soft type film forming agent.

The eye makeup composition of the present invention can simultaneously satisfy both the light usability and excellent sustainability required in a liquid oil-dispersible eye makeup formulation through a combination of highly volatile oils and a combination of a film forming agents that form a film layer which is flexible and has excellent lasting property.

Hereinafter, the present invention will be described in more detail. However, it is to be understood that in order to facilitate understanding of the present invention, the following description sets forth only the most exemplary embodiments and the scope of the present invention is not limited thereto, and the present invention encompasses all ranges equivalent to those described below.

<Hard Type Film Forming Agent>

The hard type film forming agent of the present invention may use a silicone-based film forming agent.

Generally, silicone-based resins comprising the silicone-based film forming agents can be classified into four types. Specifically, the resins are classified into M resin with one Si—O bond, D resin with two Si—O bonds, T resin with three Si—O bonds and Q resin with four Si—O bonds. The unit structure of each M, D, T, and Q resin is as follows:

M resin: $R_3SiO_{1/2}$
D resin: $R_2SiO$
T resin: $RSiO_{3/2}$
Q resin: $SiO_2$ wherein R is an alkyl group having 1 to 8 carbon atoms or an aryl group having 5 to 15 carbon atoms.

The silicone-based film forming agent of the present invention may be composed of MQ resin in which M resin and Q resin in the siloxy unit are bonded at a certain ratio. Generally, the strength of the film layer formed by the film forming agent varies depending on the ratio of M/Q constituting the resin. For example, if M/Q>1, the film layer becomes soft and weak, and conversely, if M/Q<1, the film layer becomes strong and stiff.

The M/Q ratio of the resin comprising the silicone-based film forming agent of the present invention may be preferably 0.8 or less. In the above range, the eye makeup composition of the present invention prevents the film layer from being excessively hard and easily broken, and can constitute an optimal combination with the soft type film forming agent to be described later.

Meanwhile, there are various kinds of materials that can be bonded to Si of the siloxy unit of the M resin. For example, there is an organopolysiloxane having $CH_3$ attached to Si in the M resin that is commercially used.

The silicone-based film forming agent used in the present invention may be preferably a structure in which $CH_3$ (methyl group) is bonded to the M resin comprising the silicone-based film forming agent, and specifically may be a trimethylsiloxysilicate based polymer prepared by dispersing the solid form M resin in a volatile silicone solvent together with the Q resin.

In order to facilitate understanding, the structure of trimethylsiloxysilicate, which is the hard type film forming agent that can be most preferably used in the present invention, is represented by the following Formula 1.

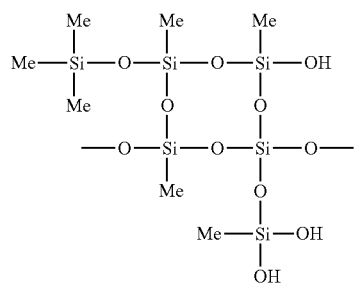

[Formula 1]

The trimethylsiloxysilicate serves particularly to provide excellent adherence and water repellency.

<Soft Type Film Forming Agent>

The soft type film forming agent imay be a silicone graft acrylic polymer-based film forming agent.

The silicone graft acrylic polymer is a polymeric material in which silicone is graft-bonded to an acrylic resin, which has an effect of enhancing the sustainability and adherence of the makeup. Specifically, the silicone graft acrylic polymer may be a copolymer form of stearyl acrylate ethylhexylacrylate for acrylic resin or a copolymer form of behenyl acrylate ethylhexylacrylate.

The silicone graft acrylic polymer-based film forming agent used as the soft type film forming agent of the present invention may preferably be, but is not limited thereto, at least one selected from the group consisting of isobutylmethacrylate/bis-hydroxypropyl dimethicone acrylate copolymer, acrylate/dimethicone copolymer, acrylate/behenylacrylate/dimethicone methacrylate copolymer, acrylate/polytrimethylsiloxymethacrylate copolymer, acrylate/bis-hydroxypropyldimethicone crosspolymer, acrylate/dimethicone methacrylate/ethylhexylacrylate copolymer, acrylate/propyltrimethicone methacrylate copolymer, acrylate/ethylhexyl acrylate/dimethicone methacrylate copolymer and acrylate/stearylacrylate/dimethicone methacrylate copolymer.

The above-mentioned hard type film forming agents and soft type film forming agents may be used in combination together.

Each of the hard type film forming agent and the soft type film forming agent of the present invention may be included in an amount of from 1 to 25 wt. %, preferably from 5 to 15 wt. %, based on the total weight of the composition. This is because when the content of each film forming agent is less than the above range, the film layer may not be formed properly, and when they all exceed the above range, the liquid formulation of the composition may not be properly formed or may be hardened easily. Also, when the content of any one film forming agent is less than or greater than the above range, an excessively hard or too damp and sticky film layer may be formed. Therefore, it is preferable to appropriately use the content of the film forming agent within the above range.

In this case, the mixing ratio of the soft type film forming agent to the hard type film forming agent is preferably from 60:40 to 30:70 by weight. When the hard type film forming agent is contained in a larger amount exceeding the above range, there arises a problem that the strength of the film layer is too hard to easily break and the surface stickiness is not exhibited. In addition, when the soft type film forming agent is contained in a larger amount exceeding the above range, the film layer is formed to be excessively soft, damp and sticky and thus does not provide a desirable feeling of use.

Conventionally, as described above, the hard type silicone-based film forming agent composed of the MQ resin polymer was used alone, and it has been difficult to simultaneously impart flexibility and hardness to the film layer as the characteristics of the film layer are directly depending on the M/Q ratio of the above-mentioned resin. However, in the present invention, the hard type film forming agent and the soft type film forming agent are also used in combination at an appropriate mixing ratio, and the M/Q ratio of the hard type film forming agent is limited to 0.8 or less, and thus a flexible and strong film layer can be formed.

<Volatile Oil>

The volatile oil used in the present invention may be preferably a volatile oil with low specific gravity. When the specific gravity of pure water at 4° C. is set to 1 as a standard material, the specific gravity of the low specific gravity volatile oil is less than 1, specifically from 0.001 to less than 1, more specifically from 0.1 to less than 1.

The volatile oil with low specific gravity may be an oil that evaporates within 1 hour upon contact with the skin or keratin fibers at room temperature and atmospheric pressure. Further, it does not contain water and an aqueous component.

The volatile oil used in the present invention may be preferably a volatile hydrocarbon oil, a volatile silicone oil or a mixture thereof.

The volatile hydrocarbon oil may be a C8-C16 branched alkane, a C8-C16 branched ester, or a mixture thereof. Examples of the C8-C16 branched alkane may be isodecane, isododecane, isohexadecane and the like as isoalkane.

Meanwhile, the volatile silicone oil may be a linear or cyclic silicone oil, and preferably, the silicone oil has a viscosity of less than or equal to 6 cSt at 25° C. The silicone oils having 2 to 5 silicon (Si) atoms may be used. More preferably, dimethicone, trisiloxane or a mixture thereof can be used.

The volatile oil may be included in an amount of from 1 to 80% by weight, specifically from 30 to 50% by weight, based on the total weight of the composition. When the content of the volatile oil is less than 1% by weight, since the amount of solvent that can disperse the film forming agents is too small, it is difficult to form a cream phase formulation suitable for use in eyebrows and to make composition with low specific gravity. When the content of the volatile oil exceeds 80% by weight, since the volatilization rate becomes too fast, there is a problem that it becomes difficult to prepare and store the composition.

The eye makeup composition of the present invention may further contain, in addition to the above-mentioned effective ingredients, ingredients such as wax, oil, powder, thickener, pigment, nutrient component, volatile solubilizer, antioxidant, preservative, fragrance and the like, which are contained in the conventional eye makeup composition, within the range not hindering the objects and effects of the present invention.

In addition, the eye makeup composition of the present invention can be utilized as a formulation such as mascara, eyeshadow, eyebrow pencil, and eyeliner. Most preferably, the composition may be a mascara or an eyeliner.

Also, the eye makeup composition of the present invention can be utilized as other makeups or all similar formulations that can be applied by applying it. For example, it can be utilized as a hair product formulation for hair styling.

Hereinafter, examples of the present invention, comparative examples and experimental examples will be described. However, the following examples, comparative examples and experimental examples are only an experimental example in relation to the constitution and effects of the present invention, and the scope and effect of the present invention are not limited thereto.

Preparation Example 1: Preparation of Eye Makeup Composition

The liquid oil-dispersible type eye makeup compositions of examples 1 and 2 and comparative examples 1 and 2 were prepared according to the prescription of the ingredient materials shown in table 1 below.

TABLE 1

| Item | Ingredient (unit: % by weight) | Example 1 | Example 2 | Comparative Example 1 | Comparative Example 2 |
|---|---|---|---|---|---|
| Wax | Polyethylene | 5 | 5 | 5 | 5 |
|  | Microcrystalline wax | 5 | 5 | 5 | 5 |
| Thickener | Disteardimonium hectorite | 5 | 5 | 5 | 5 |
| Dispersant | Polyhydroxystearic acid | 2 | 2 | 2 | 2 |
| Thickener | Propylene carbonate | 3 | 3 | 3 | 3 |
| Volatile oil | Isododecane | 50 | 30 | 50 | — |
|  | Trisiloxane | — | 20 | — | — |
| Non-volatile oil | Cyclopentasiloxane | — | — | — | 50 |
| Film forming agent (hard) | Trimethylsiloxysilicate (M/Q = 0.7) | 10 | 6 | 10 | 10 |
|  | Trimethylsiloxysilicate (M/Q = 1.3) | — | — | 10 | — |
| Film forming agent (soft) | Acrylate/dimethicone copolymer | 10 | 14 | — | 10 |
| Pigment | Black iron oxide | 10 | 10 | 10 | 10 |

Comparative example 1 was a formulation prepared by using volatile oil and only the hard type film forming agents (M/Q=0.7 and 1.3) with different M/Q ratio to each other. Comparative example 2 was a formulation prepared by using the non-volatile oil and the hard type film forming agent (M/Q=0.7) and the soft type film forming agent in combination. Examples 1 and 2 were formulations prepared by using the volatile oil, and the hard type film forming agent (M/Q=0.7) and the soft type film forming agent according to the present invention, which were specifically different in the kind and content of volatile oil, and the mixing ratio of the hard type film forming agents and the soft type film forming agents.

Experimental Example 1: Evaluation of Lightness

The degree of lightness at room temperature was evaluated for the eye makeup compositions of the comparative examples 1 and 2 and examples 1 and 2. The evaluation criteria for lightness were based on specific gravity 1, and the results are shown in table 2 below.

Measurement Method of Specific Gravity

1) A specific gravity cup of 50 id was prepared and the specific gravity cup was weighed.

2) The specific gravity cup was filled with water and measured the weight.

3) The weight of the specific gravity cup+water of 2) above was subtracted from the weight of the specific gravity cup of 1) above to calculate the weight of the water.

4) The specific gravity cup of 1) above was filled with each composition and measured the weight.

5) The weight of the specific gravity cup+composition of 4) above was subtracted from the weight of specific gravity cup of 1) above to calculate the weight of the composition.

6) The weight of the composition was divided by the weight of the water to calculate the specific gravity of the composition.

For each composition, the above-mentioned steps 1) to 6) were repeated three times to obtain the average of the results, and the results are shown in table 2 below.

TABLE 2

| Test item | Example 1 | Example 2 | Comparative example 1 | Comparative example 2 |
|---|---|---|---|---|
| Specific gravity | 0.91 | 0.88 | 0.91 | 1.08 |

In table 2, it was confirmed that the specific gravities for the examples using volatile oil are higher than that of the comparative example 2 using non-volatile oil by about 0.1~0.2.

On the other hand, when comparing comparative example 1 and example 1 which are the same in composition of the other composition including volatile oil, but differ from each other in that only the hard type film forming agent having different M/Q ratio are used, and the hard type and soft type film forming agents are used in combination, the specific gravity was the same with each other.

Meanwhile, in the case of example 2 in which the kind and content of volatile oil and hard and soft type film forming agents are different from those of example 1, it was measured to have a lower specific gravity than that of example 1 by 0.02.

Taking all the above results into account, it was identified that the kind and combination of volatile oils can directly affect specific gravity Experimental Example 2: Evaluation of the Feeling of Use For the eye makeup compositions of examples 1 and 2 and comparative examples 1 and 2, the sensory evaluation of the feeling of use about lightness, powder dropping phenomenon, sustainability, and drying speed was performed. The evaluation criteria are as follows, and the evaluation results are shown in Table 3 below.
Evaluation Criteria
⊚: Excellent, ○: Generally excellent, Δ: Usual, X: Poor

TABLE 3

| Test item | Example 1 | Example 2 | Comparative example 1 | Comparative example 2 |
|---|---|---|---|---|
| Lightness | ○ | ⊚ | ○ | Δ |
| Lowing of powder dropping phenomenon | ○ | ⊚ | X | Δ |
| Sustainability | ⊚ | ⊚ | Δ | X |
| Drying speed | ⊚ | ○ | Δ | X |

In table 3 above, it was confirmed that when compared to the comparative examples, the feeling of use of the examples was generally excellent. Particularly, when compared to comparative example 1, example 1 exhibited very good lowing of powder dropping phenomenon, sustainability and drying speed characteristics, and example 2 exhibited excellent lightness, lowing of powder dropping phenomenon and sustainability characteristics.

Also, when comparing the comparative example 2 with the examples, the feeling of use of the examples was evaluated to be significantly superior.

Taking the above results into account, it was identified that whether or not volatile oil is used and whether or not a hard type and a soft type film forming agent is combined have influence complexly on the feeling of use of the eye makeup composition.

Experimental Example 3: Comparison of Film Layer Characteristics Depending on the Mixing Ratio of the Film Forming Agents The shapes of the respective film layers prepared by different mixing ratios (weight ratios of 100:0, 70:30, 60:40, 50:50, 30:70, 0:100, respectively) of the hard type film forming agent and the soft type film forming agent are shown in comparison with the photograph of FIG. 1.

The properties of the resulting film layer produced above were evaluated according to the following evaluation criteria, and the results are shown in table 4 below.
Evaluation Criteria
(1) Strength of the Film Layer
Comparison in the state when a completely dried film layer was forced to bend.
Hard: Film was easily broken.
Soft: Film layer was drooping strengthlessly while fully bending.
When flexing up and down, because it had both flexibility and elasticity, it was evaluated by whether it was easy to bend and restore.
⊚: Easy, ○: Usually easy, Δ: Usual, X: Impossible
(2) Surface Stickiness
The film forming agent was applied at a constant thickness (100 μm), and after 10 minutes, ten pieces of paper (1*1 size) were placed on the surface of the film forming agent, and after shaking left and right five times and then dropping, the number of pieces of paper remaining on the surface was measured.
⊚: 7 or more, ○: 5~6, Δ: 3~4, X: 2 or less
(3) No Stickiness
When touching the surface of a completely dried film forming agent with a finger, it was evaluated by whether it is smooth or not.
⊚: Smooth, ○ Generally smooth, Δ Usual, X: Not smooth

TABLE 4

| | Mixing ratio | | | | | | | | |
|---|---|---|---|---|---|---|---|---|---|
| | 100:0 | 80:20 | 70:30 | 60:40 | 50:50 | 40:60 | 30:70 | 20:80 | 0:100 |
| Strength of film layer | Hard | Hard | Hard | ⊚ | ⊚ | ⊚ | ⊚ | Soft | Soft |

TABLE 4-continued

| | Mixing ratio | | | | | | | | |
|---|---|---|---|---|---|---|---|---|---|
| | 100:0 | 80:20 | 70:30 | 60:40 | 50:50 | 40:60 | 30:70 | 20:80 | 0:100 |
| Surface stickiness | X | X | X | Δ | ○ | ○ | ○ | ○ | ○ |
| No stickiness | ⊚ | ⊚ | ⊚ | ⊚ | ⊚ | ⊚ | ⊚ | ⊚ | ⊚ |

* Mixing ratio (by weight) = [Hard:Soft]

Referring to table 4, it was identified that when the combination ratio of the hard type film forming agent to the soft type film forming agent was in the range of from 60:40 to 30:70, the formed film layer had optimum strength and excellent surface stickiness and is not tacky. Particularly, within the above range, even if any mixing ratio is selected, almost the same characteristics can be maintained, and thus the optimum mixing ratio can be selected in consideration of the providing object of composition and other effects.

The invention claimed is:

1. A liquid oil-dispersible type eye makeup composition comprising:
   a volatile oil; a hard type film forming agent; and a soft type film forming agent,
   wherein the volatile oil is a volatile hydrocarbon oil, a volatile silicone oil, or a mixture thereof,
   wherein the hard type film forming agent is a silicone-based film forming agent comprising MQ resin, wherein
   M resin is represented by $R_3SiO_{1/2}$;
   Q resin is represented by $SiO_2$;
   R is an alkyl group having 1 to 8 carbon atoms or an aryl group having 5 to 15 carbon atoms; and
   said MQ resin has an M/Q ratio of 0.7 to 0.8; and
   wherein the soft type film forming agent is a silicone graft acrylic polymer-based film forming agent; and
   wherein the hard type film forming agent and the soft type film forming agent are mixed at a weight ratio of from 60:40 to 30:70.

2. The liquid oil-dispersible type eye makeup composition according to claim 1, wherein the hard type film forming agent is included in an amount of from 1 to 25% by weight, based on the total weight of the composition.

3. The liquid oil-dispersible type eye makeup composition according to claim 1, wherein the soft type film forming agent is included in an amount of from 1 to 25% by weight, based on the total weight of the composition.

4. The liquid oil-dispersible type eye makeup composition according to claim 1, wherein the volatile oil is included in an amount of from 1 to 80% by weight, based on the total weight of the composition.

5. The liquid oil-dispersible type eye makeup composition according to claim 1, wherein the silicone-based film forming agent is a trimethylsiloxysilicate-based polymer.

6. The liquid oil-dispersible type eye makeup composition according to claim 1, wherein the silicone graft acrylic polymer-based film forming agent comprises at least one selected from the group consisting of isobutylmethacrylate/bis-hydroxypropyl dimethicone acrylate copolymer, acrylate/dimethicone copolymer, acrylate/behenylacrylate/dimethicone methacrylate copolymer, acrylate/polytrimethylsiloxymethacrylate copolymer, acrylate/bis-hydroxypropyldimethicone crosspolymer, acrylate/dimethiconemethacrylate/ethylhexylacrylate copolymer, acrylate/propyltrimethicone methacrylate copolymer, acrylate/ethylhexyl acrylate/dimethiconemethacrylate copolymer and acrylate/stearylacrylate/dimethiconemethacrylate copolymer.

7. The liquid oil-dispersible type eye makeup composition according to claim 1, wherein the volatile oil evaporates within 1 hour at room temperature and atmospheric pressure upon contact with skin or keratin fibers.

8. The liquid oil-dispersible type eye makeup composition according to claim 1, wherein the volatile hydrocarbon oil is C8-C16 branched alkane, C8-C16 branched ester, or a mixture thereof.

9. The liquid oil-dispersible type eye makeup composition according to claim 1, wherein the volatile silicone oil is dimethicone, trisiloxane, or a mixture thereof.

* * * * *